US006390985B1

(12) United States Patent
Mamayek

(10) Patent No.: US 6,390,985 B1
(45) Date of Patent: May 21, 2002

(54) IMPEDANCE MATCHING TRANSDUCERS

(75) Inventor: Don S. Mamayek, Mountain View, CA (US)

(73) Assignee: SCIMED Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/358,496

(22) Filed: Jul. 21, 1999

(51) Int. Cl.[7] .................................................. A61B 8/12

(52) U.S. Cl. ........................ 600/459; 310/336; 29/25.35

(58) Field of Search ................................. 600/437, 439, 600/459, 462–467; 73/642, 644; 310/334–336, 368

(56) References Cited

U.S. PATENT DOCUMENTS

| | | | | |
|---|---|---|---|---|
| 2,833,999 A | * | 5/1958 | Howry | 340/8 |
| 4,572,981 A | * | 2/1986 | Zola | 310/357 |
| 5,045,746 A | * | 9/1991 | Wersing et al. | 310/334 |
| 5,164,920 A | | 11/1992 | Bast et al. | 367/140 |
| 5,359,760 A | * | 11/1994 | Busse et al. | 29/25.35 |
| 5,410,208 A | * | 4/1995 | Walters et al. | 310/334 |
| 5,553,035 A | * | 9/1996 | Seyed-Bolorforosh et al. | 367/140 |
| 5,855,049 A | * | 1/1999 | Corbett, III et al. | 29/25.35 |

FOREIGN PATENT DOCUMENTS

| | | | |
|---|---|---|---|
| EP | 0 355 694 | 2/1990 | B06B/1/06 |
| EP | 0 629 993 | 12/1994 | G10K/11/02 |

OTHER PUBLICATIONS

Draheim et al., Finite Element and Experimental Study of Impedance Matching Layer Optimization, *Proc. SPIE*, vol. 3037, Apr. 1997, pp. 135–139.

Haller et al., Micromachined Acoustic Matching Layers, *Proc. SPIE*, vol. 1733, Nov., 1992, pp. 72–77.

W. A. Smith, New Opportunities in Ultrasonic Transducers Emerging from Innovations in Piezoelectric Materials, *SPIE Proceedings*, vol. 1733, (1992), pp. 3–24.

Wallace Arden Smith et al., Modeling 1–3 Composite Piezoelectrics, Thickness–Mode Oscillations, *IEEE Transactions of U. S.*, vol. 38, No. 1, Jan. 1991, pp. 40–47.

Pedersen, Tretiak & He, Impedance Matching Properties of an Inhomogeneous Matching Layer with Continuously Changing Acoustic Impedance, *J. Accoustical Society of America*, (1982) vol. 72, No. 2, pp. 327–336.

* cited by examiner

*Primary Examiner*—Francis J. Jaworski
(74) *Attorney, Agent, or Firm*—Townsend and Townsend and Crew, LLP

(57) ABSTRACT

The present invention provides exemplary transducer elements, transducer packages and methods of making same. One exemplary transducer element (10) has first and second transducer surfaces (14, 20) and a plurality of tapered pillars (16) that comprise piezoelectric material and extend between the first and second transducer surfaces. At least one of the pillars has a first cross-sectional area at the first transducer surface that is larger than a second cross-sectional area at the second transducer surface. Hence, the transducer has a lower acoustic impedance at the second surface than at the first surface.

38 Claims, 5 Drawing Sheets

FIG. 6A
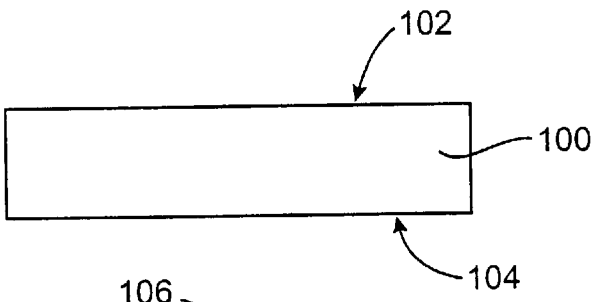
FIG. 6B
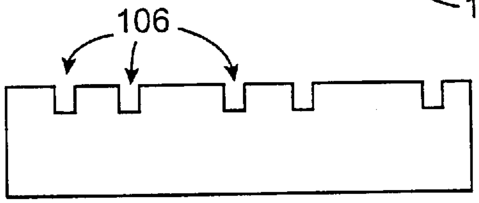
FIG. 6C
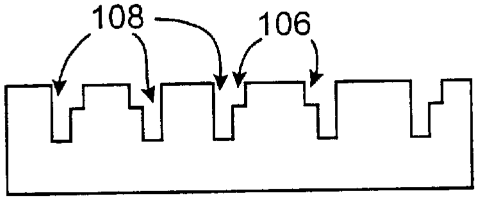
FIG. 6D
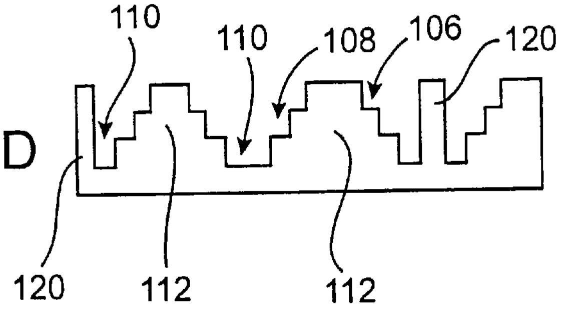
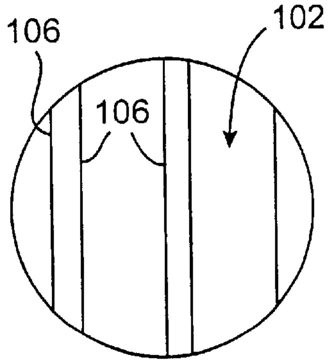
FIG. 6E
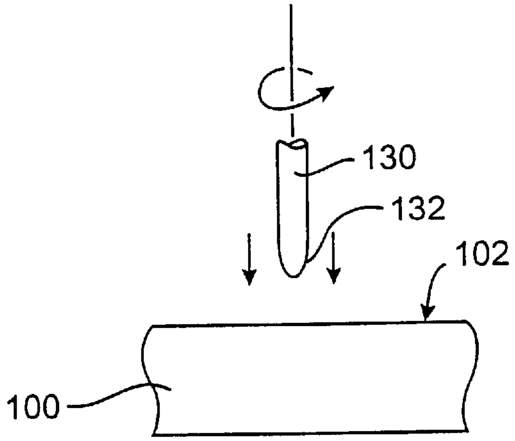
FIG. 7

IMPEDANCE MATCHING TRANSDUCERS

BACKGROUND OF THE INVENTION

The present invention relates generally to ultrasonic imaging catheters, and more particularly, to improved transducers for use in ultrasonic imaging catheters.

Intravascular imaging of blood vessels and surrounding tissues continues to be of great benefit in a wide range of medical fields. A particularly successful design for an intravascular imaging catheter employs a rotatable imaging assembly containing an ultrasonic transducer, where the assembly is attached to the distal end of a flexible drive cable. The transducer may be rotated within a catheter body or sheath in order to transmit an ultrasonic signal and produce a video image by well-known techniques. The transducer element or elements are connected to electronics, typically maintained outside the patient's body, to produce the video image.

When a sound wave generated by a typical transducer impinges on an interface between two different media, such as the interface between the transducer face and the tissue being imaged, part of the incident wave is reflected and part is transmitted. The amount of wave reflected compared to the amount transmitted depends primarily on the relative acoustic impedances of the two media at the media interface. For some transducers, this difference can be quite large. For example, the acoustic impedance of a atypical piezoelectric transducer is about 30 mRayls, and the acoustic impedance of tissue is about 3 mRayls. In general, it is desirable to reduce or minimize the difference in acoustic impedance between the two media to permit a greater amount of the ultrasound wave to transmit through the interface.

In order to reduce the impedance mismatch between the transducer and tissue, some existing catheters attach one or more matching layers to the transducer face which have an acoustic impedance between that of the transducer and that of the tissue being imaged. In general, having a greater number of interfaces, each with a small acoustic impedance mismatch, is more desirable than a single interface having a large impedance mismatch.

Another technique involves using transducers made from piezocomposite material. In these transducers, the piezoelectric material is mixed with non-piezoelectric material to reduce the transducer's overall acoustic impedance. For example, as shown in FIG. 1, a prior art transducer 200 has a plurality of columns 210 made from piezoelectric material interspersed with a plurality of columns 220 made from non-piezoelectric material.

While this transducer has achieved some degree of success, it is desirable to provide a piezoelectric transducer having a better acoustic impedance profile to provide better acoustic impedance matching with tissue or the matching layer. It is further desirable to provide impedance matching without greatly increasing the number of interfaces the ultrasound signals must cross.

SUMMARY OF THE INVENTION

The present invention provides improved ultrasound transducers, transducer packages, and methods of making same. The transducer packages of the present invention are intended to overcome at least some of the problems of the prior art, and will be particularly useful for ultrasound imaging catheters. For example, transducer elements and packages of the present invention are designed to reduce the acoustic impedance at the imaging surface of the transducer.

Such transducers hence provide better acoustic impedance matching, and have improved performance.

In one embodiment, the present invention provides an exemplary transducer element for use in an imaging catheter. The transducer element has first and second transducer surfaces defining a thickness therebetween. The transducer includes a plurality of tapered pillars that comprise piezoelectric material and extend between the first and second transducer surfaces. At least one of the pillars has a first cross-sectional area at the first transducer surface that is larger than a second cross-sectional area at the second transducer surface. In this manner, the pillar has an increasingly smaller cross-sectional area as it tapers away from the first transducer surface.

In one aspect, the transducer element further includes a backing material operably attached to the first transducer surface. Similarly, in one aspect the transducer element further includes a matching layer operably attached to the second transducer surface.

In one particular aspect, the transducer element further includes a filler material disposed between the pillars and defining a portion of the second transducer surface. In one aspect, the filler material also defines a portion of the first transducer surface. Alternatively, the plurality of pillars merge together to completely define the first transducer surface. In this manner, the first transducer surface is completely defined by piezoelectric material.

Preferably, the filler material is selected from a group of materials consisting essentially of epoxy, gel, plastic, air, combinations of such materials such as epoxy with air bubbles, and the like. Such filler materials have a lower acoustic impedance than an acoustic impedance of the pillars.

In one aspect, the first cross-sectional area of at least one of the pillars has a shape that is generally rectangular. In another aspect, the first cross-sectional area of at least one of the pillars has a shape selected from a group of shapes consisting of a square, a rectangle, a circle, an ellipse and an oval. Preferably, at least one of the pillars has a sloped outer surface that is positioned at a non-perpendicular angle to the second transducer surface. In this manner, the pillar tapers away from the first transducer surface and has a smaller cross-sectional area further from the first transducer surface.

In another embodiment, the present invention provides a transducer element having a base which defines a first transducer surface. The transducer element includes a plurality of columns extending from the base. The columns comprise piezoelectric material, and each column has an upper surface. The upper surfaces of the columns collectively define a first portion of a second transducer surface. At least one of the columns has a first cross-sectional area at the base that is larger than a second cross-sectional area at the second transducer surface.

In one aspect, the transducer element further includes a filler material disposed between the plurality of columns and defining a second portion of the second transducer surface. Preferably, the second portion of the second transducer surface is larger than the first portion. In this manner, the second transducer surface is defined by more filler material than column material. In one aspect, the transducer has a first acoustic impedance at the base that is greater than a second acoustic impedance at the second transducer surface. In one particular aspect, the base includes a piezoelectric material, such as a piezoplastic, piezoceramic and the like.

The present invention further provides a transducer package for use in an imaging catheter. The transducer package includes a transducer having a base. The base defines a first transducer surface. A plurality of pillars extend from the base and comprise piezoelectric material. Each of the pillars has an upper surface, with the upper surfaces collectively defining a first portion of a second transducer surface. At least one of the pillars has a first cross-sectional area at the base that is larger than a second cross-sectional area at the upper surface. The transducer package further includes a backing material operably attached to the first transducer surface.

In one aspect, the transducer package further includes a filler material disposed between the pillars and defining a second portion of the second transducer surface. Together, the pillar upper surfaces and filler material completely define the second transducer surface.

The present invention further provides methods of making transducers and transducer packages, particularly for use in imaging catheters. In one particular embodiment, a method of the present invention includes the steps of providing a transducer element having first and second spaced apart surfaces defining a transducer element thickness therebetween. The transducer element comprises piezoelectric material having a first acoustic impedance. The method includes removing a portion of the transducer element to create a plurality of pillars extending between the first and second surfaces. At least one of the pillars has a first cross-sectional area at the first surface that is larger than a second cross-sectional area at the second surface. The method includes placing a filler material between the plurality of pillars. The filler material has a second acoustic impedance that is less than the first acoustic impedance. In this manner, the second surface is made up of more filler material than is the first surface. As a result, the second surface has a lower acoustic impedance than the first surface.

In one aspect, the plurality of pillars merge together to completely define the first surface. In one particular aspect, the removing step includes cutting a portion of the transducer element with a cutting apparatus and removing that portion. In one aspect, the removing step creates at least one of the pillars to be a tapered pillar. The tapered pillar has a cross-sectional area that increases as the tapered pillar extends away from the second surface. Alternatively, the plurality of pillars comprises a plurality of tapered pillars.

In one aspect, the removing step creates the plurality of pillars to have a stair-step tapered shape. In another aspect, the removing step creates a plurality of gaps at the first surface between the plurality of pillars. In this manner, the filler material defines part of the first surface.

In one aspect, the method further includes the step of mounting a backing material to the first transducer surface. Preferably, the backing material is a sound-attenuating material. In one aspect, the mounting step occurs prior to the removing step. For example, mounting the backing material to the first transducer surface before the removing step may be desirable when the removing step will create gaps at the first surface between the plurality of pillars.

In another method of the present invention, a transducer element is provided which includes piezoelectric material having a first acoustic impedance. A portion of the transducer element is removed to create a base portion of the transducer element and a plurality of pillars extending from the base portion. The base portion defines a first transducer surface. The plurality of pillars each have an upper surface, and at least one of the pillars has a first cross-sectional area at the base portion that is larger than a second cross-sectional area at the upper surface. The method includes adhering a filler material between the plurality of pillars. The filler material has a second acoustic impedance that is lower than the first acoustic impedance. The filler material and the plurality of pillar upper surfaces define a second transducer surface.

In still another method of the present invention, a piezoelectric material is provided and formed into a desired shape having a base portion and a plurality of pillars. In one aspect, the forming step includes molding the piezoelectric material. This can be accomplished, for example, by injection molding, press molding, casting, and the like.

Other features and advantages of the invention will appear from the following description in which the preferred embodiment has been set forth in detail in conjunction with the accompanying drawings.

BRIEF DESCRIPTION OF THE DRAWINGS

FIGS. 6–6D depict side views of a method of making transducer elements according to the present invention;

FIG. 6E depicts a top view of the transducer element depicted in FIG. 6B; and FIG. 7 depicts an alternative method of creating pillars according to the present invention.

DESCRIPTION OF THE SPECIFIC EMBODIMENTS

Figure 1:
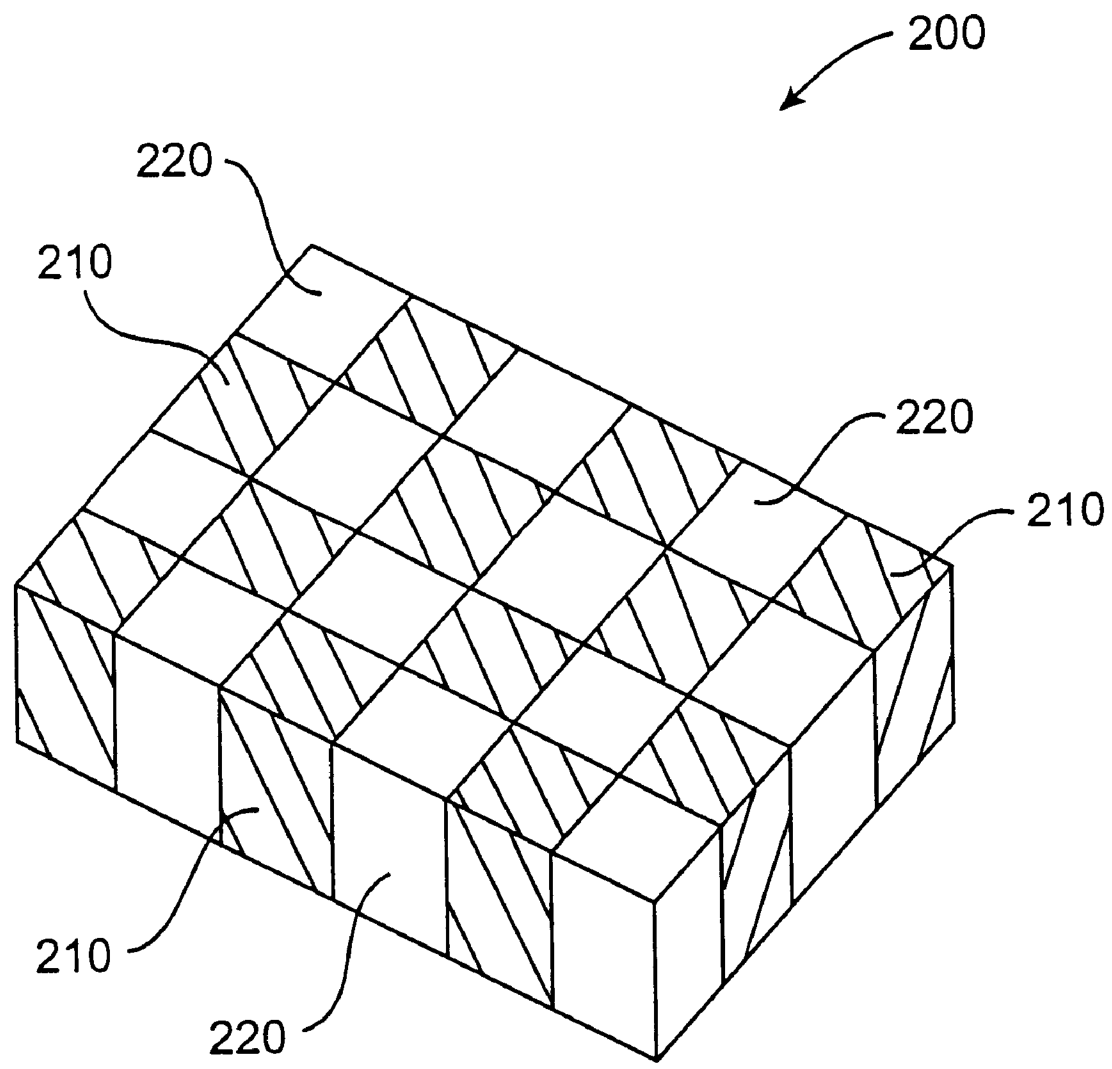
(PRIOR ART) FIG. 1
FIG. 1 depicts a prior art transducer element.
Figure 2A:
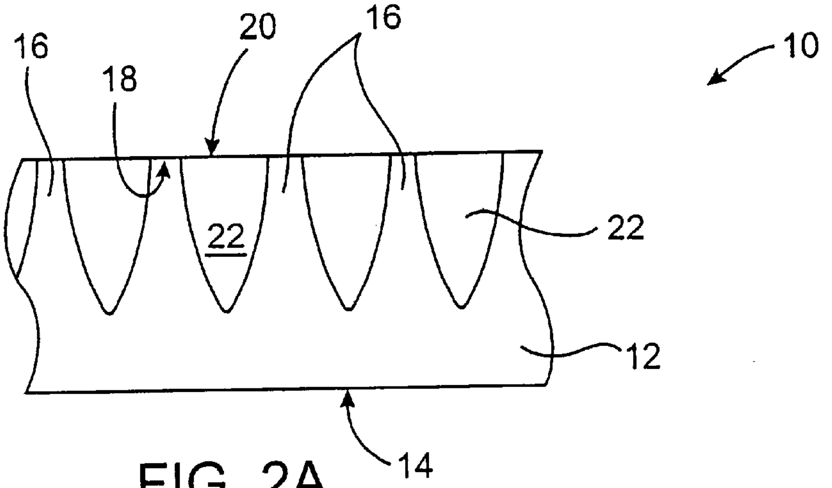
FIGS. 2A–2C depict a side view, an overall view, and an overall view with a portion of the filler material removed, respectively.
Figure 2B:
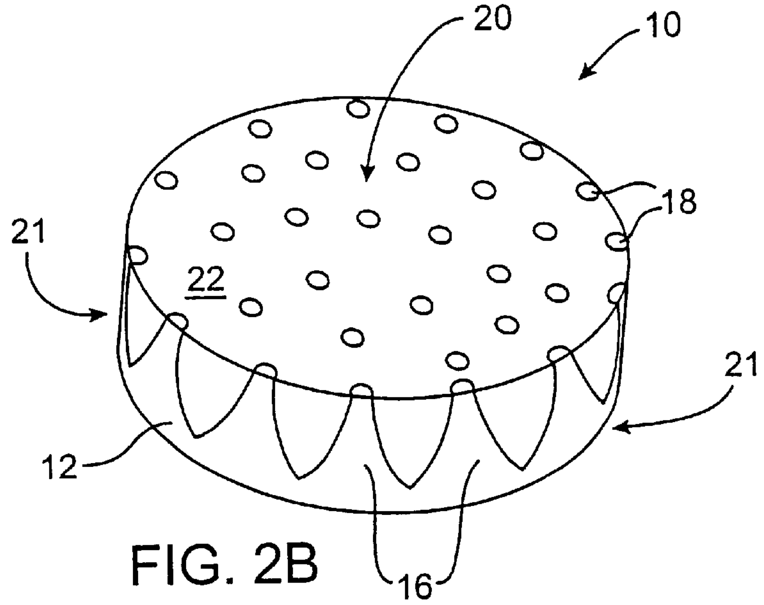
Figure 2C:
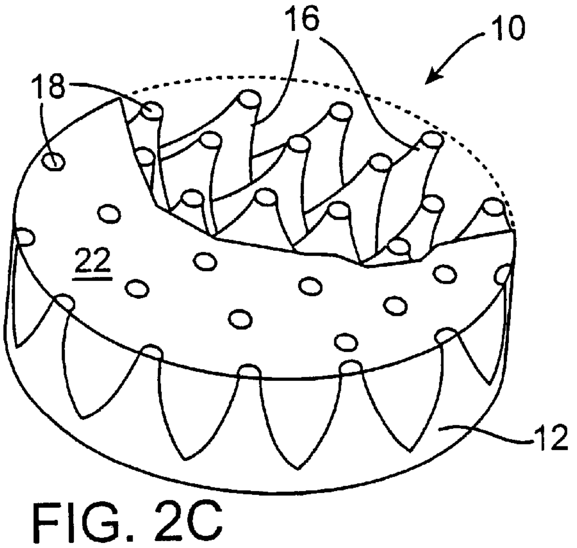

FIGS. 2–2C depict an exemplary transducer element 10 according to the present invention. FIG. 2A depicts a side view of transducer element 10 having a base or base portion 12 defining a first transducer surface 14. A plurality of pillars 16, preferably tapered pillars 16, extend from base 12. A filler material 22 is disposed between pillars 16. Upper surfaces 18 of pillars 16 and filler material 22 collectively define a second transducer surface 20. As shown in FIGS. 2–2C, pillars 16 of the present invention preferably have a smaller cross-sectional area closest to second transducer surface 20. Hence, pillars 16 preferably taper away from base 12.

Preferably, pillars 16 and base 12 comprise a piezoelectric material. For example, piezoelectric material may include piezoceramics (such as PZT), piezoplastics and the like. Filler material 22 can be a wide range of materials within the scope of the present invention. For example, filler material 22 may include epoxy, gel, plastics, air, combinations of these materials such as epoxy or gel with air bubbles, and the like. Preferably, filler material 22 has an acoustic impedance that is less than an acoustic impedance of pillars 16. In this manner, the overall acoustic impedance of transducer element 10 at second surface 20 is less than the overall acoustic impedance of transducer element 10 at first surface 14. By aligning second transducer surface 20 to be closest to the tissue being imaged, or to a matching layer (not shown), the acoustic mismatch at the interface is reduced. Hence, a greater percentage of ultrasound signals generated by transducer 10 will enter the tissue as opposed to being reflected by the interface.

The overall views shown in FIGS. 2B and 2C further emphasize details of exemplary transducer element 10. While transducer 10 is depicted to be generally circular or elliptical, it will be appreciated by those skilled in the art that transducer 10 can have a variety of shapes within the scope of the present invention. For example, transducer element 10 could comprise a generally rectangular, square or other shaped transducer element. Further, transducer element 10 may be a plurality of transducer elements, such as an annular array. Exemplary annular arrays are described in U.S. patent application Ser. No. 09/017,581, entitled "Annular Array Ultrasound Catheter," the complete disclosure of which is incorporated herein by reference.

FIG. 2B depicts transducer element 10 showing second surface 20 defined by filler material 22 and upper surfaces 18 of pillars 16. In one embodiment, greater than fifty percent of second surface 20 is defined by filler material 22. The size of pillars 16 at second surface 20 can be varied for different transducer elements 10, to provide the desired acoustic impedance at second surface 20. By way of example, in some instances it may be preferable to have second surface 20 defined almost entirely by filler material 22, and in other instances it may be preferable to have more than fifty percent of second surface 20 defined by pillars 16.

As shown in FIG. 2C, which depicts transducer element 10 with a portion of filler material 22 removed for convenience of illustration, pillars 16 extend from base 12 towards second transducer surface 20 in a manner which provides decreasing cross-sectional areas for at least some pillars 16. One advantage of the present invention is that the acoustic impedance at second transducer surface 20 is less than the acoustic impedance at base 12 or first transducer surface 14, due in large part to the reduction of piezoelectric materials at second transducer surface 20 compared to the amount of piezoelectric material at base 12 or first transducer surface 14.

In the embodiment having air as filler material 22, it is desirable to have the periphery 21 of transducer element 10 comprise piezoelectric material or other material. In the manner, a matching layer (not shown) or other layer can be placed on second surface 20. The matching layer in conjunction with periphery 21 acts to seal air into the space between pillars 16. Such a configuration helps prevent the wicking of fluid between pillars 16 when transducer element 10 is used in an aqueous environment, such as in a patient vasculature.

Figure 3A:
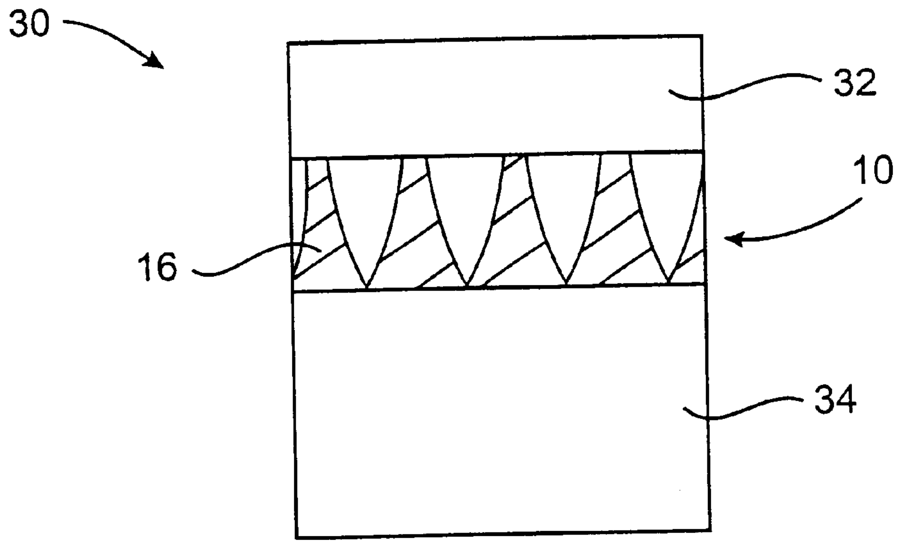
FIGS. 3A–3B depict side views of alternative transducer packages according to the present invention.
Figure 3B:
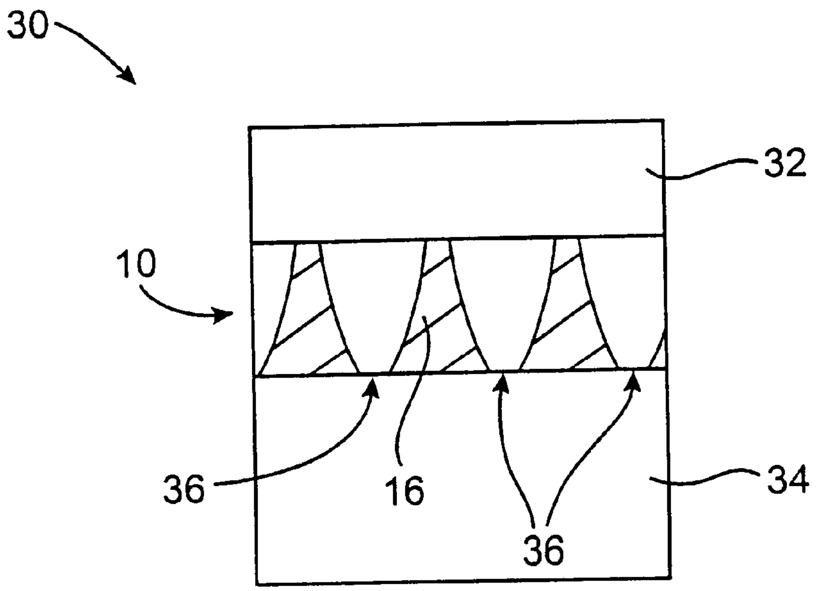

Turning now to FIGS. 3A and 3B, alternative embodiments of the present invention will be described. FIGS. 3–3B depict a transducer package 30 having transducer element 10 sandwiched between a matching layer 32 and a backing material 34.

Matching layer 32 may comprise a wide range of materials, including both electrically conductive and electrically non-conductive materials. Matching layer 32 operates to provide impedance matching effects between transducer element 10 and tissue to be imaged. Exemplary matching layers are further described in U.S. patent application Ser. No. 09/358,495, entitled "Off-Aperture Electrical Connect Transducer and Methods of Making," the complete disclosure of which is incorporated herein by reference. It will be appreciated by those skilled in the art that one or more matching layers, or alternatively no matching layers, may be used within the scope of the present invention.

Backing material 32 similarly can comprise a wide range of materials including electrically conductive material, such as epoxy, silver/tungsten epoxy or the like, or electrically non-conductive material, such as epoxy, polyurethane, rubber or the like. It will be appreciated by those skilled in the art that matching layers and backing material can similarly be used in conjunction with other embodiments of the present invention, including that shown in FIG. 2.

As shown in FIGS. 3–3B, transducer element 10 does not have base 12 in these embodiments. In the embodiment shown in FIG. 3A, pillars 16 merge to completely define first transducer surface 14. In this manner, transducer element 10, upon receipt of an electrical signal, converts the electrical signal into an ultrasound wave which propagates out from second transducer surface 20, through matching layer 32 and into surrounding tissue or fluids to be imaged. Ultrasound signals generated by pillars 16 (or in the case of the embodiment shown in FIG. 2, base 12) are propagated out into backing material 34. Backing material 34 is designed to have sound attenuating properties therein to reduce the effect of artifacts.

Alternatively, as shown in FIG. 3B, transducer element 10 has no base 12 and further has pillars 16 that do not completely define first transducer surface 14. In this embodiment, filler material 22 partially defines both first transducer surface 14 and second transducer surface 20.

Figure 4A:
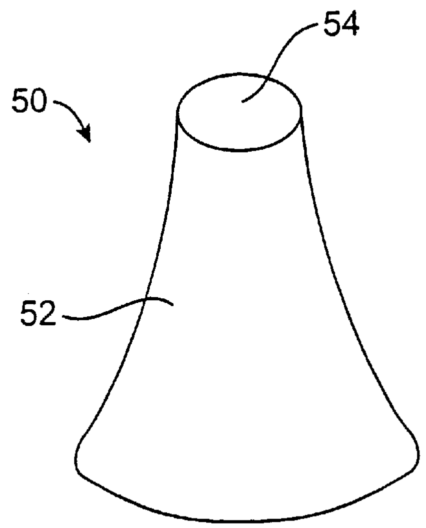
FIGS. 4A–4C depict overall views of exemplary tapered pillars according to the present invention.
Figure 4B:
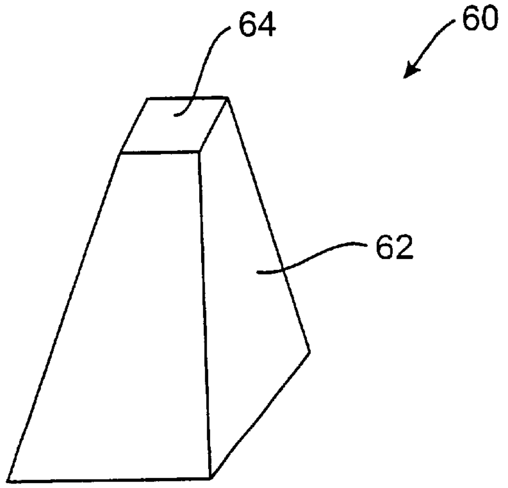
Figure 4C:
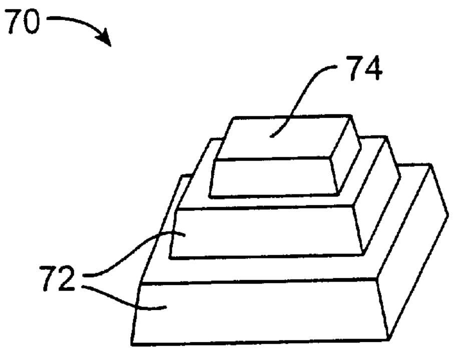
Figure 4D:
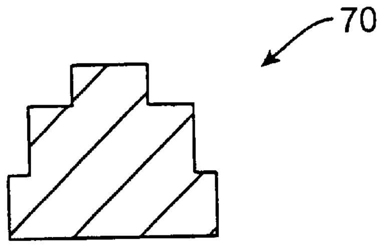
FIG. 4D depicts a side cross-sectional view of the pillar depicted in FIG. 4C.

Turning now to FIGS. 4–4D, exemplary pillars for use in the present invention will be described. In general, pillars 16 may take a variety of shapes provided that at least one or more pillars 16 are tapered to provide a wider cross-sectional area near first transducer surface 14 compared to pillar 16 cross-sectional area near or at second transducer surface 20. For example, as shown in FIG. 4A, a pillar 50 may be used having a generally circular or elliptical upper surface 54. In this particular embodiment, pillar 50 has an outer surface 52 with a sloped or curved shape. For example, outer surface 52 may have a generally gaussian-shaped or other desired curvature. The cross-sectional area of pillar 50 increases as pillar 50 slopes away from upper surface 54. It will be appreciated by those skilled in the art that upper surface 54 can have, for example, a generally circular shape and still permit pillar 50 to have a generally elliptical or other shaped cross-sectional area further removed from upper surface 54.

Alternatively, a pillar 60 may have a generally square or rectangular cross-sectional area such as that shown in FIG. 4B. In this manner, an upper surface 64 typically would have, but need not have, a square or rectangular cross-sectional area. Pillar 60 has an outer surface 62 that is depicted as generally flat and positioned at an angle relative to upper surface 64. Alternatively, surface 62 can be curved similar to surface 52. The size of cross-sectional area of pillar 60 again decreases as pillar 60 tapers toward upper surface 64.

In still another embodiment, a pillar 70 has a generally stair-step tapered outer surface 72. In such an embodiment, an upper surface 74 preferably is square or rectangular, although surface 74 could also be circular, oval, elliptical or other shapes. As shown in the cross-sectional view in FIG. 4D, outer surface 72 has a generally stair-step shape and the cross-sectional area of pillar 70 increases as pillar 70 stair-steps away from upper surface 74. While pillar 70 may not provide as smooth an acoustic matching effect as pillar 50 or pillar 60, pillar 70 may be easier to manufacture as described in conjunction with FIG. 6.

Figure 5A:
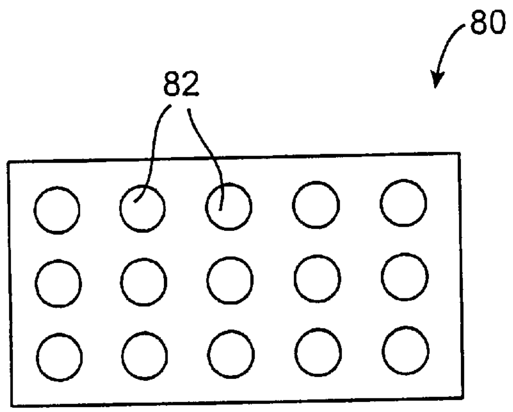
FIGS. 5A–5B are top views of alternative transducer elements according to the present invention.
Figure 5B:
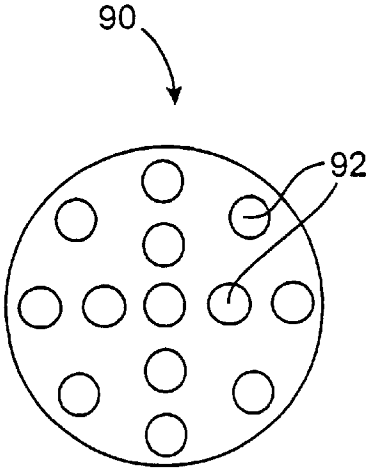

As shown in FIGS. 5A and 5B, the orientation of pillars within transducer elements of the present invention, can have a variety of configurations. For example, as shown in FIG. 5A, a transducer element 80 has a generally rectangular shape. A plurality of pillar upper surfaces 82 are shown having a generally uniform distribution. Alternatively, as shown in FIG. 5B, a transducer element 90 may have a plurality of pillars configured therein such that a plurality of pillar upper surfaces 92 are arranged in a generally radial pattern. It will be appreciated by those skilled in the art that the two pillar configurations depicted in FIGS. 5A and 5B may be interchanged between transducers 80 and 90, and represent just two of a wide range of pillar configurations within the scope of the present invention. Further, the pillars need not be formed in a symmetrical pattern as depicted in FIG. 5, but can be formed in an asymmetrical pattern.

Turning now to FIGS. 6–E, a method of manufacturing a transducer element 100 according to the present invention will be described. Transducer element 100 is provided having a second surface 102 and a first surface 104. As shown in FIG. 6B, a first series of cuts 106 are made in second surface 102 to a pre-determined depth and at predetermined locations. As shown in FIG. 6E, cuts 106 preferably are generally straight and extend across the entire second surface 102 of transducer element 100. Cuts 106 operate to remove a portion of transducer element 100 material. It will be appreciated by those skilled in the art that a generally circular shape transducer element 100 depicted in FIG. 6E is one of a wide range of shapes for transducer element 100 within the scope of the present invention.

As shown in FIG. 6C, a second series of cuts 108 are made in a manner such that cuts 108 are slightly deeper than and adjacent to cuts 106. Again, cuts 108 operate to remove material from transducer 100. FIG. 6D depicts a third series of cuts 110 made in transducer 100. Third series of cuts 110 are made adjacent to and slightly deeper than second series of cuts 108. In one aspect, cuts 110 extend between about 60 percent and about 95 percent of the way through transducer element 100, although other cut 110 depths also are anticipated within the scope of the present invention. One way of forming base portion 12 is by not having the deepest cuts extend completely through transducer element 100. Alternatively, the deepest cuts can extend all the way through transducer element 100 thickness, preferably after first affixing transducer element 100 to a backing layer to provide stability.

In this manner, a plurality of tapered pillars 112 are formed in transducer element 100 by removing the material that has been cut away as described in FIG. 6B–6D. It will be appreciated by those skilled in the art that cuts 106–110 can be made in a different order than that described above, and that a larger or smaller number of cuts can be made to form tapered pillars 112 within the scope of the present.

Further, the method of forming tapered pillars 112 also can be used to form one or more generally vertical sided or non-tapered pillars 120. In this manner, depending upon the number and spacing desired, plurality of tapered pillars 112 and plurality of non-tapered pillars 120 may be formed in the same transducer element 100.

Cuts 106–110 can be created in a variety of ways. For example, cuts 106–110 may be formed using a laser such as an excimer laser, a cutting apparatus such as a saw or drill, a knife, and the like. Further, cuts 106–110 may be formed by other processes such as etching, ion milling, photolithography techniques, moulding, and the like.

As shown in FIG. 7, a drill 130 may be used to form tapered pillars within transducer element 100. In this method, drill 130 has a drill tip 132 with a desired shape. For example, drill tip 132 may have a generally gaussian shape to form pillars 112 in transducer element 100 having a desired gaussian-shaped outer surface. In this manner, drill 130 is inserted into transducer element 100 to the proper depth to form plurality of pillars 112. It will be appreciated by those skilled in the art that the techniques for removing portions of transducer element 100 to form pillars 112, 120 need not be mutually exclusive. For example, some pillars within transducer element 100 may have a stair-step tapered shape, such as that shown in FIGS. 4C and 6D, and other pillars in transducer element 100 can have different shapes, such as those shown in FIGS. 4–4B.

As previously described, the present invention provides exemplary methods of making transducers for use in imaging catheters. Preferably, the methods include providing transducer elements which include piezoelectric material having a first acoustic impedance. Typically, the first acoustic impedance of the piezoelectric material is greater than the acoustic impedance of tissue or fluids to be imaged. The method includes the steps of removing a portion of the transducer element to create the plurality of pillars extending between either the first and second transducer surfaces, or between the base portion of the transducer element and the transducer element second surface. Preferably, at least one, and sometimes all, pillars formed within the transducer element have a tapered shape which presents a smaller cross-sectional area closest to the imaging surface of the transducer element, described herein as the second transducer surface. A filler material is provided and adhered between the plurality of pillars. Filler material preferably forms a portion of the second transducer surface and, depending upon the particular embodiment, may form a portion of the first transducer surface.

In an alternative method, piezoelectric material is provided and formed into transducer element 100 having the desired shape. This can be accomplished, for example, by providing a mold or cast to mold the piezoelectric material, including pillars 112, 120, into the desired shape to form transducer element 100. An injection mold, a press mold, or other molds may be used within the scope of the present invention. The space between pillars 112, 120 can then be filled with filler material.

The invention has now been described in detail. However, it will be appreciated that certain changes and modifications may be made. For example, transducer packages may comprise more than one matching layer. Further, methods of removing transducer material include positioning the second transducer surface 102 at a desired angle relative to the cutting apparatus to create tapered pillars. Therefore, the scope and content of this invention are not limited by the foregoing description. Rather, the scope and content are to be defined by the following claims.

What is claimed is:

1. A transducer element for use in an imaging catheter comprising:

first and second transducer surfaces defining a thickness therebetween; and a plurality of tapered pillars comprising piezoelectric material extending between said first and second transducer surfaces;

at least one of said pillars having a first cross-sectional area at said first transducer surface that is larger than a second cross-sectional area at said second transducer surface, said at least one pillar comprising a curved pillar surface between said first and second transducer surfaces.

2. A transducer element as in claim 1, further comprising a backing material operably attached to said first transducer surface.

3. A transducer element as in claim 1, further comprising a matching layer operably attached to said second transducer surface.

4. A transducer element as in claim 1, further comprising a filler material disposed between said pillars and defining a portion of said second transducer surface.

5. A transducer element as in claim 4, wherein said filler material further defines a portion of said first transducer surface.

6. A transducer element as in claim 4, wherein said filler material is selected from a group of materials consisting essentially of epoxy, gel, plastics, air, and combinations thereof.

7. A transducer element as in claim 4, wherein said filler material has a filler material acoustic impedance that is less than an acoustic impedance of said pillars.

8. A transducer element as in claim 4 wherein said filler material defines greater than fifty percent (50%) of said second transducer surface.

9. A transducer element as in claim 1, wherein said plurality of pillars merge together to completely define said first transducer surface.

10. A transducer element as in claim 1, wherein said first cross-sectional area of at least one of said pillars has a shape that is generally rectangular.

11. A transducer element as in claim 1, wherein said first cross-sectional area of at least one of said pillars has a shape selected from a group of shapes consisting of a square, a rectangle, a circle, an ellipse and an oval.

12. A transducer element as in claim 1, wherein at least one of said pillars has a sloped outer surface that is positioned at a non-perpendicular angle to said second transducer surface.

13. A transducer element for use in an imaging catheter comprising:

a base portion defining a first transducer surface; and a plurality of columns comprising piezoelectric material extending from said base portion;

each of said columns having an upper surface, said upper surfaces defining a first portion of a second transducer surface, wherein said first portion is less than fifty percent (50%) of said second transducer surface;

at least one of said columns having a first cross-sectional area at said base portion and a second cross-sectional area at said upper surface, wherein said first-cross sectional area is larger than said second cross-sectional area said at least one column having a non-linear taper between said base portion and said upper surface.

14. A transducer element as in claim 13, further comprising a filler material disposed between said plurality of columns and defining a second portion of said second transducer surface.

15. A transducer element as in claim 13, wherein said transducer has a first acoustic impedance at said base portion and a second acoustic impedance at said second transducer surface, said first acoustic impedance being greater than said second acoustic impedance.

16. A transducer element as in claim 13, wherein said base portion comprises a piezoelectric material.

17. A transducer element as in claim 13 wherein said at least one column comprises a curved pillar surface between said first and second transducer surfaces.

18. A transducer package for use in an imaging catheter comprising:

a transducer having a base defining a first transducer surface; and a plurality of pillars extending from said base, said pillars comprising piezoelectric material;

each of said pillars having an upper surface, said upper surfaces defining a first portion of a second transducer surface;

at least one of said pillars having a first cross-sectional area at said base and a second cross-sectional area at said upper surface, wherein said first-cross sectional area is larger than said second cross-sectional area, said at least one pillar comprising a curved pillar surface between said first and second transducer surfaces; and a backing material operably attached to said first transducer surface.

19. A transducer package as in claim 18, further comprising a filler material disposed between said plurality of pillars and defining a second portion of said second transducer surface.

20. A transducer package as in claim 18 wherein said filler material defines greater than fifty percent (50%) of said second transducer surface.

21. A transducer package as in claim 18 wherein said curved surface comprises a gaussian surface.

22. A method of making a transducer for use in an imaging catheter comprising:

providing a transducer element comprising piezoelectric material having a first acoustic impedance, said transducer element having first and second spaced apart surfaces defining a transducer element thickness therebetween;

removing a portion of said transducer element to create a plurality of pillars extending between said first and second surfaces;

wherein at least one of said pillars has a first cross-sectional area at said first surface that is larger than a second cross-sectional area at said second surface, said at least one pillar comprising a curved pillar surface between said first and second transducer surfaces; and placing a filler material between said plurality of pillars, said filler material having a second acoustic impedance that is less than said first acoustic impedance.

23. A method as in claim 22, wherein said plurality of pillars merge together to completely define said first surface.

24. A method as in claim 22, wherein said removing comprises cutting said portion of the transducer element with a cutting apparatus and removing said portion.

25. A method as in claim 22, wherein said removing creates at least one of said pillars to be a tapered pillar, said tapered pillar having a cross-sectional area that increases as said tapered pillar extends away from said second surface.

26. A method as in claim 22, wherein said plurality of pillars comprises a plurality of tapered pillars.

27. A method as in claim 22, wherein said removing creates a plurality of gaps at said first surface between said plurality of pillars.

28. A method as in claim 22, further comprising mounting a backing material to said first transducer surface.

29. A method as in claim 28, wherein said mounting occurs prior to said removing.

30. A method as in claim 22 wherein said removing comprises removing between about sixty percent (60%) and about ninety-five percent (95%) of a thickness of said transducer element to define said plurality of pillars.

31. A method of making a transducer for use in an imaging catheter comprising:

providing a transducer element comprising piezoelectric material having a first acoustic impedance;

removing a portion of said transducer element to create a base portion of said transducer element and a plurality of pillars extending from said base portion, said base portion defining a first transducer surface and said plurality of pillars each having an upper surface;

wherein at least one of said pillars has a first cross-sectional area at said base portion that is larger than a second cross-sectional area at said upper surface; and adhering a filler material between said plurality of pillars, said filler material having a second acoustic impedance that is less than said first acoustic impedance, and said filler material and said plurality of pillar upper surfaces defining a second transducer surface, said at least one pillar having a non-linear taper between said base portion and said upper surface and wherein said filler defines greater than fifty percent (50%) of said second transducer surface.

32. A method as in claim 31 wherein said plurality of pillars comprise at least two different shapes of said pillars.

33. A method as in claim 31 wherein said plurality of pillars are in an asymmetrical pattern.

34. A method of making a transducer for use in an imaging catheter comprising:

providing a piezoelectric material having a first acoustic impedance;

forming said piezoelectric material into a desired shape, said desired shape comprising a base portion defining a first transducer element surface; and a plurality of pillars extending from said base portion, said plurality of pillars each having an upper surface;

wherein at least one of said pillars has a first cross-sectional area at said base portion that is larger than a second cross-sectional area at said upper surface, said at least one pillar comprising a curved pillar surface between said first and second transducer surfaces; and adhering a filler material between said plurality of pillars, said filler material having a second acoustic impedance that is less than said first acoustic impedance, and said filler material and said plurality of pillar upper surfaces defining a second transducer element surface.

35. A method as in claim 34, wherein said forming comprises molding said piezoelectric material.

36. A transducer element as in claim 1 wherein said plurality of tapered pillars extend through between about sixty percent (60%) and about ninety-five percent (95%) of a thickness of said transducer element.

37. A transducer element as in claim 1 wherein said plurality of pillars comprise at least two different shapes of said pillars.

38. A transducer element as in claim 1 wherein said plurality of pillars are in an asymmetrical pattern.

* * * * *